United States Patent

Handelsman et al.

[11] Patent Number: 5,695,982
[45] Date of Patent: Dec. 9, 1997

[54] CANAVANINE RESISTANT STRAINS OF BACILLUS CEREUS

[75] Inventors: Jo Handelsman; Jocelyn Louise Milner; Elizabeth Anne Blackson, all of Madison, Wis.

[73] Assignee: Wisconsin Alumni Research Foundation, Madison, Wis.

[21] Appl. No.: 705,445

[22] Filed: Aug. 29, 1996

[51] Int. Cl.[6] ............................ C12N 1/20; C12Q 1/04; A01N 63/00
[52] U.S. Cl. ................................ 435/252.5; 435/252.1; 435/3.4; 424/93.46
[58] Field of Search ........................... 435/252.5, 252.1, 435/34, 172.1; 424/93.46

[56] References Cited

U.S. PATENT DOCUMENTS

| 4,877,738 | 10/1989 | Handelsman et al. | 424/93.46 |
| 5,543,301 | 8/1996 | Handelsman et al. | 435/34 |

Primary Examiner—Jean C. Witz
Assistant Examiner—Susan Hanley
Attorney, Agent, or Firm—Quarles & Brady

[57] ABSTRACT

Biocontrol strains of the bacterial species *Bacillus cereus* have been previously identified as having use in aiding the growth of crop plants, but have suffered from inconsistent performance on alfalfa. It has been found that biocontrol *B. cereus* strains are inhibited by canavanine, an analogue of arginine exuded by alfalfa seeds. It has also been found that canavanine resistant mutant strains of *B. cereus* biocontrol strains can readily be made in culture which exhibit the ability to grow in the presence of alfalfa seed and inhibit Pythium pathogenesis.

5 Claims, No Drawings

CANAVANINE RESISTANT STRAINS OF BACILLUS CEREUS

FIELD OF THE INVENTION

The present invention relates to the use of microbes in agriculture in general and relates, in particular, to the use of bacterial strains as biocontrol agents in field applications to help the growth of crop plants.

BACKGROUND OF THE INVENTION

A focus of research activity in recent years has been the use of biological agents to increase agricultural productivity and efficiency. Biological control, or biocontrol, is the use of microorganisms to suppress plant pests or to supplement plant growth. Biocontrol methods and agents are believed to offer an attractive alternative to chemical pesticides and fungicides which are less favored than they may have been in the past because of concerns about human health and environmental quality. A variety of programs have used screening and other methods to isolate biological agents from the environment which are effective in the field to combat pests or to facilitate the growth of crop plants.

An example of a biological control agent into which significant scientific and economic development has occurred is *Bacillus thuringiensis*. It was discovered that *B. thuringiensis* strains produce toxic proteins which have the ability to specifically kill targeted insects. The initial discovery of the efficacy of *B. thuringiensis* strains as insecticides led to a significant research effort which later identified a large number of *B. thuringiensis* strains which exhibit a variety of target ranges and efficacies.

Another species of Bacillus from which strains with biocontrol activity have been identified is the species *Bacillus cereus*. Several *Bacillus cereus* strains have been found to have specific biocontrol efficacy to facilitate the growth of crop plants. One specific strain of *Bacillus cereus*, which has been referred to both as UW85, and by its ATCC designation 53522, has been demonstrated to have biocontrol efficacy in field applications with many crops. The *B. cereus* strain UW85 was found to protect alfalfa seedlings from damping off caused by *Phytophthora medicaginis*, tobacco seedlings from *Phytophthora nicotianae*, cucumber fruits from rot caused by *Pythium aphanidermatum*, and peanuts from *Sclerotinia minor*. UW85 is also described in U.S. Pat. No. 4,877,738 where it is identified by reference to its ATCC accession number, 53522. It was later found that UW85 produced two antifungal compounds which contribute independently to the suppression of damping off fungi, due to the antifungal and antibacterial activity of these two compounds.

As used herein, "biological control" or "biocontrol" is meant to refer to the suppression of a pathogen by use of a biological organism. The mechanisms of biological control are diverse and often poorly understood. It is possible that the control may be achieved by competition between the introduced bacteria and the fungi for space on the surface of the plant roots. It is also possible, and likely in the instance of Bacillus cereus strains, that the biocontrol strain produces toxins which are inhibitory to the growth of the pathogenic fungi.

The UW85 *Bacillus cereus* strain has been used in a wide variety of field applications. In particular, it has been found that the strain offers best biological control activity on a variety of legume plants in field applications, notably on soybean. However, the results of the application of UW85 in field applications to alfalfa have not been as consistent. The reason for the difference in consistency of result between use of UW85 on soybean and alfalfa was heretofore not known.

SUMMARY OF THE INVENTION

The present invention is summarized and has been found that *Bacillus cereus* biocontrol strains are inhibited in their growth in the presence of alfalfa seeds by the effect of canavanine, an arginine analogue, naturally exuded by the seeds of alfalfa. The present invention is further summarized in that it has been found that mutant *Bacillus cereus* strains that are resistant to canavanine can be created using bacteriological techniques, and therefore the mutants are more likely to be capable of colonizing the seeds of alfalfa than the native strains of *Bacillus cereus*.

It is therefore an object of the present invention to create refined and improved biocontrol strains of *Bacillus cereus* which are capable of growing in the presence of alfalfa seeds to foster the growth of alfalfa plants and suppress plant pathogenic diseases such as the root rots.

It is a feature of the present invention that a method is described for creating new strains of canavanine resistant mutants of *Bacillus cereus* biocontrol strains, which are therefore better adapted for use in alfalfa.

Other objects, advantages, and features of the present invention will become apparent from the following specification.

DETAILED DESCRIPTION OF THE INVENTION

The present invention was intended to improve the consistency of result from the application of *Bacillus cereus* biocontrol strains to alfalfa crops under field conditions. The reason for less consistent results from the application of *Bacillus cereus* biocontrol strains to alfalfa, as compared to other legume plants, was obscure prior to the research described herein. The research described below led to the realization that the growth of *Bacillus cereus* strains in conjunction with alfalfa was inhibited by canavanine exuded by the alfalfa. Canavanine is an analog of the amino acid arginine, more particularly the guanidinooxy analog of arginine, and is a common secondary metabolite of legume plants. Canavanine synthesis and translocation patterns within the plants suggest that this amino acid serves as a storage component of nitrogen and is rapidly utilized by young seedlings. Canavanine therefore also tends to be present in the seedling at higher concentrations than other parts of the mature plant.

Canavanine has also been found to be toxic to some microbial species. The mechanism of canavanine toxicity may involve replacement of arginine by the analog, i.e. canavanine, in protein synthesis producing non-functional substituted enzymes which fail to support important biochemical mechanisms in the cell. Some microorganisms are clearly sensitive to canavanine, although the full extent of the canavanine sensitivity for a given microorganism can only be determined by empirical testing.

It was found here, it is believed for the first time, that the actual agent responsible for inhibition of *Bacillus cereus* growth in alfalfa seeds was canavanine. It was further discovered that it is possible to select mutants of useful *Bacillus cereus* biocontrol strains, which mutants are then resistant to the effect of canavanine. In such a manner, it is now possible to create improved biocontrol mutant *B. cereus* strains which have better utility for use on alfalfa in particular, and canavanine-producing legumes in general.

The observation which gave rise to the research described herein began by the observation that there were more variable yields with alfalfa fields treated with *Bacillus cereus* strain UW85 as compared to the experience in soybean. Soybean does not produce canavanine. The investigation began by examining alfalfa seed exudate to better understand the relationships between the chemicals present in the exudate and the biocontrol bacteria. Structural analysis were conducted on various inhibitory fractions obtained from alfalfa seed exudates to determine which molecules from those fractions were those particularly responsible for the inhibition of the growth of *Bacillus cereus* biocontrol strain. For that analysis, *Bacillus cereus* strain UW85 was used. Structural analysis of the inhibitory material purified from the alfalfa seed exudate identified canavanine as a molecule responsible for the inhibitory effect. It was also discovered that while the growth of UW85 was inhibited by alfalfa seed exudate on minimal media, the inhibitory effect was prevented by the addition to the media of arginine, histidine, or lysine. These three amino acids were also capable of preventing inhibition caused by the direct addition of canavanine to growing cultures of *Bacillus cereus* UW85. After screening a diverse collection of microorganisms, it was determined that only a few strains of microorganisms, notably *Bacillus cereus*, *Bacillus thuringiensis*, *Pythium torulosum*, and *Vibrio cholerae*, were inhibited by alfalfa seed exudates. The profile of microorganisms which are sensitive to the alfalfa seed exudate mimicked precisely the profile of microorganisms which also were sensitive, in laboratory assay, to canavanine. The amount of canavanine present in alfalfa seed exudates and the sensitivity of the microorganism to canavanine, whether from alfalfa or introduced from purified sources, demonstrated conclusively that canavanine was the operative agent in the inhibition of UW85 by alfalfa root exudates.

Like all microorganisms maintained in cultures for extended periods, UW85, and other biocontrol *Bacillus cereus* strains, are subject to a certain spontaneous mutation rate. This rate is not so high as to rapidly alter useful strains. For example, UW85 has been maintained in cultures since, as its name implies, 1985, without obvious mutation. It was found that when a culture of UW85 was continuously exposed to canavanine, spontaneous mutants which were resistant to canavanine were selected. The growth rates and sensitivities of the various mutants varied within a certain range, but the mutants appeared at a significant and practical frequency without the addition of mutagenizing compounds or radiation. The mutants that were identified could then be tested for wild-type growth rates and antibiotic sensitivities, and characterized by biological control activities, to make sure that the essential activities of biocontrol agents associated with the useful strains were not lost to the mutant strains. This analysis revealed that mutant strains could readily be identified that, in laboratory tests, retain full biocontrol activity and other morphological and identifying characteristics of UW85, but were mutant strains in the sense that they now possess an additional characteristic, that characteristic being the increased resistance to the presence of canavanine in the culture medium.

The method of creating canavanine-resistant mutants described here will enable mutants of biocontrol strains of *Bacillus cereus* to be created which are more consistently useful on alfalfa. Biocontrol strains of *Bacillus cereus* can be isolated by the method described in U.S. Pat. No. 5,543,301 to Handelsman et al., the disclosure of which is hereby incorporated by reference. After identification of a biocontrol *B. cereus* strain, the canavanine resistant mutants can be selected by exposure to canavanine as described below. Following mutation, the mutant strains should be tested for retained biocontrol efficacy. A laboratory test on alfalfa is also described below. Hence, the creation of canavanine resistant strains from a variety of *B. cereus* biocontrol strains becomes possible.

It is noteworthy that the mutant biocontrol *B. cereus* strains thus created have a practical resistance to canavanine sufficient so as to be useful biocontrol agents in the presence of alfalfa seeds. This practical level of canavanine resistance can be achieved by cultivation of *B. cereus* strains on media containing canavanine on the order of 100–200 µg/ml of culture medium. It has been found that *B. cereus* strains resistant to canavanine at this level are competent to exhibit biocontrol activity in the presence of alfalfa seeds in a manner that the corresponding native canavanine-sensitive parental strain was not.

After mutant canavanine-resistant strains have been created, it is, as stated above, helpful to re-test the strains for biocontrol activity to ensure that the phenotype Of biocontrol activity is not lost in the mutant strains. While a field test is ultimately the most determinative test, laboratory tests have been found to provide a reasonable predictor of field efficacy. Since the purpose of this method is to create biocontrol strains effective consistently in alfalfa, it is suggested that the most relevant biocontrol test is also on alfalfa. Described below is a laboratory test using alfalfa seeds. This laboratory test is useful, predictive and not burdensome to perform. As the results below will indicate, the canavanine-resistant mutant strains are more effective than their parental wild-type strain for biocontrol of Pythium in the presence of alfalfa seeds. Thus, this test both verifies the retention of the biocontrol phenotype in the mutant strains as well as demonstrating the superiority of the mutants for the alfalfa target crop.

EXAMPLES

Inhibition of UW85 by alfalfa seed and seed exudate

In exploring the interaction between *B. cereus* strain UW85 and alfalfa, it was discovered that alfalfa seeds placed on a minimal media, MESAA1 media (Milner et al., *Appl. Microbiol. Biotech.*, 43:685 (1995) inhibited the growth of UW85, while similar seeds placed on a rich medium did not inhibit the growth of UW85. The inhibition of growth of UW85 on MESAA1 medium by alfalfa seeds was prevented by addition of arginine, histidine or lysine to the medium. The timing of release of the inhibitory factor from the seed varied among the alfalfa cultivars tested, but seeds from all nine germplasm groups of alfalfa proved to inhibit the growth of UW85.

Fractions of exudate of the alfalfa seeds were analyzed. The alfalfa seed exudate was prepared by the method used in Milner et al., supra. The inhibitory fractions typically eluted from an HPLC column 18 to 25 minutes after sample injection. The $^1$H-NMR spectrum of the inhibitory fractions ($D_2O$) exhibited only three signals: a two-proton multiplet at 3.96 ppm, a one-proton doublet of doublets at 3.86 ppm, and a two-proton multiplet at 2.21 ppm. The five resonances in the $^{13}$C-NMR spectrum consisted of two $sp^2$ (177.4, 161.4 ppm) and three $sp^3$-hybridized carbons (72.6, 55.8, 32.5 ppm). The electrospray ionization (ESI) mass spectrum suggested a protonated molecular weight of 177, and the high-resolution fast-atom bombardment (HRFABMS) mass spectrum gave the molecular formula $C_5H_{13}N_4O_3$ ($[M+H]^+$ m/z 177.098400, observed; 177.098765 calculated) consistent with the NMR data. The COSY spectrum indicated the carbon skeleton=CH—CH$_2$—CH$_2$—X, and heteronuclear correlations from HMQC and HMBC spectra led to an initial partial structure. It was further reasoned that because the molecular formula required three more nitrogen atoms and one oxygen atom than the initial partial structure contained, and because the chemical shift of C-4 (72.6 ppm) required a C-O band, the remaining sp$^2$ carbon must exist as an oxoguanidine. Based on this analysis, the inhibitor factor was found to be the 5-oxa analogue of arginine, or canavanine, a substance previously identified in the seeds of leguminous plants. Barron et al., *Physiol. Plant Path.*, 11:305–311 (1977); Felton et al., *Jour. Invert. Path.*, 44:187–191 (1984).

In performing the above analysis, the inhibitory fraction was purified from crude seed extract first by the addition of activated carbon and filtration. The exudate was concentrated by evaporation under reduced pressure to a small volume and three parts cold ethanol were added to one part seed exudate to precipitate macromolecules. The mixture was incubated at −20° C. overnight and then centrifuged. The supernatant was evaporated so that 1 ml represented 8g of seed and extracted with phenol and chloroform. The aqueous portion was resuspended in sterile distilled water so that 1 ml exudate represented material from 3.0 g seed, adjusted with concentrated HCl to pH 6.0, and filtered through a 0.22 µm filter. This material was subjected to HPLC.

The HPLC analysis was performed on a Beckman model 322 system equipped with a 10 mm×25 cm Ultrasphere cyano column running at a flow rate of 2 ml per minute. 750 µl of a seed exudate (representing material exuded from 2.25 g seed) was injected each run. Fractions were collected every minute for thirty minutes. The initial solvent conditions were 100% water and five minutes after sample injection, a 45-minute gradient to 100% 20 mM ammonium acetate was initiated.

Quantification studies, not further described here in detail, were performed to determine the amount of canavanine present in alfalfa seed exudate. It was determined that exudate from 1 g of Iroquois alfalfa seed contained 44 µg of canavanine.

Studies of Canavanine Inhibition

To study the effect and range of canavanine inhibition, bacteria were grown on MESAA1 solid medium, supra, with D,L-malic acid as the carbon source. Bacteria were grown on MESAA1 plates for 48 hours at 28° C. before zones of inhibition were measured. Seeds were surface disinfected in 18 M sulfuric acid and rinsed with sterile distilled water. Release of the inhibitory material from the seeds was monitored by testing bacterial inhibition by samples of exudate removed at 50-minute intervals after initiation of shaking.

A series of microorganisms were tested in parallel for sensitivity to both alfalfa seed exudate and to a commercial preparation of canavanine. The results are summarized in the following Table 1. The zones of inhibition in Table 1 were determined using a radial streak assay on MESAA1 minimal media after incubation at 28° C. for two to three days and are expressed in mm±a standard deviation. The profile of microorganisms sensitive to alfalfa seed exudate clearly mimics the profile of microorganisms sensitive to canavanine.

TABLE 1

| Organism and Strain Tested | Inhibition Zone Seed Exudate | Inhibition Zone Canavanine |
|---|---|---|
| *Agrobacterium tumefaciens* K759 | 0 | 0 |
| *Aureobacterium saperdae* LP19 | 0 | 0 |
| *Bacillus cereus* UW85 | 23.3 ± 2.0 | 17 ± 0 |
| *Bacillus cereus* ALF 115 | 0 | 0 |
| *Bacillus thuringiensis* HD1 | 14.5 ± 0.7 | 19.5 ± 0.7 |
| *Bacillus thuringiensis* 4E1 | 0 | 0 |
| *Escherichia coli* K37 | 0 | 0 |
| *Erwinia herbiceula* LS005 | 0 | 0 |
| *Klebsiella pneumoniae* 8030 | 0 | 0 |
| *Pseudomonas aureofaciens* 30–84 | 0 | 0 |
| *Pseudomonas fluorescens* 2–79 | 0 | 0 |
| *Pythium torulosum* A25a zoospores | 15 ± 7.1 | not tested |
| *Rhizobium meliloti* 1021 | 0 | 0 |
| *Rhizobiuin tropici* 899 | 0 | 0 |
| *Salmonella typhimurium* LT2 | 0 | 0 |
| *Vibrio cholerae* F115A | 25.5 ± 3.5 | 27.5 ± 2.1 |

In performing the radial streak assay for the data above, a well containing 50 µl seed exudate or 5 µg of commercial canavanine was placed in the center of a MESAA1 plate, and bacteria were streaked out from the well. The sensitivity of oomycete pathogens was determined by spreading zoospores of the pathogen on MESAA1 plates containing wells of 50 µl crude seed exudate. *Pythium torulosum* zoospores were prepared by transferring a plug of mycelium to a V8 agar plate, allowing the mycelium to grow for 7 days, flooding the plate with sterile water (20 ml) for 30 minutes, discarding the water, cutting the agar in half and transferring one-half to an empty Petri dish. Zoospores, released after 8–12 hours, were diluted to a concentration of 10$^4$ zoospores per ml.

It was further found that inhibition of UW85, tested by the plate method, was prevented by the addition of certain amino acids. All twenty amino acids were tested by adding each amino acid separately in powder form to a filter disk on MESAA1 medium spread on a lawn of UW85. Canavanine inhibition of UW85, and alfalfa root exudate inhibition of UW85, were both prevented by the addition of arginine, histidine, or lysine.

Generation of Canavanine resistant mutants

To investigate if canavanine resistant mutants would arise spontaneously, single colonies of UW85 were inoculated into 2 ml of brain heart infusion broth (BHI), grown overnight at 28° C., and 100 µl of the overnight culture was plated on MESAA1 supplemented with 150 µg/ml of L-canavanine. Only one mutant from each MESAA1 plate was selected for further study. The growth rate and sensitivity to various antibiotics were examined for each mutant, and four mutants with wild type growth rates and antibiotic sensitivities were found.

The canavanine-resistant mutants were found to arise at a frequency of 10$^{-8}$. No mutagenic agent or radiation was required. Mutant cultures which exhibited growth and antibiotic sensitivity characteristics identical to the parental strain were readily isolated. Four of the canavanine-resistant mutant strains of UW85 were designated UW2000, UW2001, UW2002, and UW2003. These strains were selected for biocontrol assays.

Testing of resistant strains

A laboratory test was designed to verify that the biocontrol capability of the canavanine-resistant mutants was retained. In this test, Magnum III alfalfa seeds were surface-disinfected in 18M sulfuric acid as described by Milner et al. supra, and coated with water, UW85, or one of the canavanine-resistant mutants. Bacterial cultures for seed coating were grown at 28° C. for four days in half-strength tryptic soy broth (TSB) to ensure sporulation. Cells were spun down and the cell pellet was resuspended in 1/20th volume of supernatant, so that cells were concentrated twenty fold. Seeds were placed in disposable pipette tips (200 μl volume) and tips were placed in tip boxes that had been punctured and fitted into a vacuum line. Concentrated cell suspensions or water were applied from above into each tip containing seeds. Seeds were then soaked with the cell suspension or water for 3 minutes and then the seeds were vacuum-treated. Seeds from each treatment were sonicated for 30 seconds, the sonicate was diluted, and dilutions of sonicate were plated on 0.1 strength tryptic soy agar (TSA) to determine the bacterial colony-forming units (cfu's) per seed. Standard F1020 flats (Hummert International) with inserts containing 96 compartments per insert were filled up to 1 cm from the top with sterile vermiculite. One coated seed was placed in each compartment. Each flat was filled with 4 L of deionized water. Zoospores of Pythium were prepared as described above and added to the 4 L of water so that the final concentration in the flat was 0, 1000, or 1500 zoospores per seed. Sterile vermiculite was added to fill each compartment completely. Flats were placed in a 24° C. growth chamber with a photoperiod of 12 hours and were watered daily to maintain a constant water level. Root length was measured 13 days after inoculation with zoospores.

The results of these assays are presented below in Table 2. Each mean value represents 16 seeds (4 seeds per replicate and 4 replicates). The larger the root length, the healthier the plant. A zero indicates that the plant did not emerge from the seed.

TABLE 2

|  | Mean | Std. Error |
|---|---|---|
| Condition 1 | | |
| No Pythium | | |
| UW 2001 | 52.13 | 9.01 |
| UW 2002 | 54.84 | 4.51 |
| UW 2003 | 42.75 | 4.60 |
| UW 2000 | 62.94 | 4.93 |
| UW 85 | 48.69 | 5.23 |
| Water | 61.36 | 1.75 |
| Condition 2 | | |
| 1000 zoospores per seed | | |
| UW 2001 | 23.25 | 6.25 |
| UW 2002 | 8.13 | 4.71 |
| UW 2003 | 11.69 | 4.42 |

TABLE 2-continued

|  | Mean | Std. Error |
|---|---|---|
| UW 2000 | 17.81 | 12.05 |
| UW 85 | 0.00 | 0 |
| Water | 0.00 | 0 |
| Condition 3 | | |
| 1500 Zoospores per seed | | |
| UW 2001 | 10.00 | 6.23 |
| UW 2002 | 5.38 | 5.38 |
| UW 2003 | 18.75 | 7.39 |
| UW 2000 | 31.13 | 7.76 |
| UW 85 | 0 | 0 |
| Water | 0 | 0 |

We claim:

1. A method of making a biocontrol strain of *Bacillus cereus* for use on alfalfa comprising
    (a) identifying a biocontrol strain of *Bacillus cereus*;
    (b) culturing the biocontrol strain of *Bacillus cereus* in a medium containing canavanine in an amount effective to achieve canavanine resistance;
    (c) selecting bacterial strains capable of growth in said medium;
    (d) verifying that said selected biocontrol strains of *Bacillus cereus* retain the biocontrol activity of the strain of step (a).

2. The method of claim 1 wherein the verifying step is performed on alfalfa seedlings or seeds.

3. The method of claim 1 wherein the medium used in the culturing step is a minimal medium.

4. A biologically pure culture of a biocontrol strain of *Bacillus cereus* which is capable of growth in a medium containing canavanine in an amount effective to achieve canavanine resistance, produced by the method comprising
    (a) identifying a biocontrol strain of *Bacillus cereus*;
    (b) culturing the biocontrol strain of *Bacillus cereus* in a medium containing canavanine in an amount effective to achieve canavanine resistance;
    (c) selecting bacterial strains capable of growth in said medium;
    (d) verifying that said selected biocontrol strains of *Bacillus cereus* retain the biocontrol activity of the strain of step (a).

5. The biologically pure strain of claim 4 which inhibits the growth of Pythium fungi on alfalfa.

* * * * *

UNITED STATES PATENT AND TRADEMARK OFFICE
CERTIFICATE OF CORRECTION

PATENT NO. : 5,695,982
DATED : December 9, 1997
INVENTOR(S) : Jo Handelsman, Jocelyn Louise Milner, Elizabeth Anne Blackson It is certified that error appears in the above-identified patent and that said Letters Patent is hereby corrected as shown below:

Column 1, after the title insert the following:

--This invention was made with United States government support awarded by the following agencies: USDA, Grant #92-34190-6941 (thru Purdue Agreement No: 593-0130-16). The United States has certain rights in this invention.--

Signed and Sealed this

Seventh Day of April, 1998

Attest:

BRUCE LEHMAN

Attesting Officer

Commissioner of Patents and Trademarks